(12) United States Patent
Salit et al.

(10) Patent No.: US 11,492,459 B2
(45) Date of Patent: *Nov. 8, 2022

(54) RUBBER COMPOSITION

(71) Applicant: COMPAGNIE GENERALE DES ETABLISSEMENTS MICHELIN, Clermont-Ferrand (FR)

(72) Inventors: Anne-Frédérique Salit, Clermont-Ferrand (FR); Benoît Schnell, Clermont-Ferrand (FR); Sophie Gander, Clermont-Ferrand (FR); Sergey Ivanov, Clermont-Ferrand (FR); Etienne Fleury, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 236 days.

This patent is subject to a terminal disclaimer.

(21) Appl. No.: 16/762,758

(22) PCT Filed: Nov. 20, 2018

(86) PCT No.: PCT/FR2018/052916
§ 371 (c)(1),
(2) Date: May 8, 2020

(87) PCT Pub. No.: WO2019/102131
PCT Pub. Date: May 31, 2019

(65) Prior Publication Data
US 2020/0362139 A1   Nov. 19, 2020

(30) Foreign Application Priority Data
Nov. 21, 2017  (FR) ...................... 1760959

(51) Int. Cl.
*C08K 5/1515*   (2006.01)
*B60C 1/00*     (2006.01)
*B60C 11/00*    (2006.01)
*C07D 303/20*   (2006.01)

(52) U.S. Cl.
CPC .......... *C08K 5/1515* (2013.01); *B60C 1/0016* (2013.01); *B60C 11/0008* (2013.01); *C07D 303/20* (2013.01); *B60C 2011/0025* (2013.01)

(58) Field of Classification Search
CPC . C08K 5/1515; B60C 1/0016; B60C 11/0008; B60C 2011/0025; C07D 303/20
USPC ......................................... 524/114
See application file for complete search history.

(56) References Cited

U.S. PATENT DOCUMENTS

| | | | |
|---|---|---|---|
| 2012/0046418 A1* | 2/2012 | Seo | C08F 8/48 525/333.1 |
| 2013/0123418 A1 | 5/2013 | Araujo Da silva et al. | |
| 2014/0114025 A1* | 4/2014 | Brandau | C08K 5/0091 526/273 |
| 2016/0251456 A1* | 9/2016 | Ugolnikov | C08C 19/22 525/281 |
| 2018/0194787 A1 | 7/2018 | Ivanov et al. | |

FOREIGN PATENT DOCUMENTS

WO   2017009150 A1   1/2017

OTHER PUBLICATIONS

International Search Report and Written Opinion corresponding to PCT/FR2018/052916 dated Apr. 9, 2019.

* cited by examiner

*Primary Examiner* — Doris L Lee
(74) *Attorney, Agent, or Firm* — Dickinson Wright PLLC

(57) ABSTRACT

A rubber composition based on at least one diene elastomer, a reinforcing filler and a 1,3-dipolar compound comprising an epoxide group is provided. The epoxide group is a 3-membered ether ring in which a first member is a carbon atom exhibiting a connection to the dipole of the 1,3-dipolar compound and a second member is a tertiary or quaternary carbon. Such a rubber composition exhibits improved properties at break and an improved processing, as well as good hysteresis properties.

20 Claims, No Drawings

RUBBER COMPOSITION

This application is a 371 national phase entry of PCT/FR2018/052916 filed on 20 Nov. 2018, which claims benefit of French Patent Application No. 1760959, filed 21 Nov. 2017, the entire contents of which are incorporated herein by reference for all purposes.

BACKGROUND

1. Technical Field

The field of the present invention is that of diene rubber compositions reinforced by a filler which can be used in particular in the manufacture of tyres for vehicles.

2. Related Art

It is known to introduce 1,3-dipolar compounds into diene rubber compositions during the preparation of the latter. Reference may be made, for example, to Patent Application WO 2012007442. It is described therein that 1,3-dipolar compounds typically react with the diene elastomers of the rubber composition. The reactivity of the dipole of the 1,3-dipolar compound with regard to the diene elastomers makes it possible to graft functional groups on the diene elastomers of the rubber composition It is also known to use, in rubber compositions, diene elastomers modified in that they bear pendent glycidyl groups. Such elastomers are, for example, described in Patent Application US 2012/0046418 A1 and are obtained by the reaction of a 1,3-dipolar compound bearing a glycidyl group. However, it turns out that the elastomers thus modified confer, on the rubber composition which contains them, degraded properties at break.

In point of fact, a crosslinked rubber composition has to exhibit good properties at break in order to be able to be used in a semi-finished article for a tyre. This is because, during rolling, the tyre is subjected to high stresses and to great strains, it being known that it also has to exhibit the lowest possible rolling resistance.

SUMMARY

The Applicant Company has discovered, surprisingly, that a rubber composition comprising a 1,3-dipolar compound bearing a specific substituted epoxide group exhibits improved properties at break and an improved processing, as well as good hysteresis properties.

A first subject-matter of the invention is a rubber composition based on at least one diene elastomer, a reinforcing filler and a 1,3-dipolar compound comprising an epoxide group, the epoxide group being a 3-membered ether ring in which a first member is a carbon atom exhibiting a connection to the dipole of the 1,3-dipolar compound and a second member is a tertiary or quaternary carbon.

Another subject-matter of the invention is a tyre which comprises a rubber composition in accordance with the invention.

The invention also relates to a process for manufacturing a rubber composition in accordance with the invention.

I. DETAILED DESCRIPTION

In the present description, unless expressly indicated otherwise, all the percentages (%) shown are % by weight.

The abbreviation "phr" means parts by weight per hundred parts of elastomer (of the total of the elastomers, if several elastomers are present).

Furthermore, any interval of values denoted by the expression "between a and b" represents the range of values greater than "a" and less than "b" (that is to say, limits a and b excluded), whereas any interval of values denoted by the expression "from a to b" means the range of values extending from "a" up to "b" (that is to say, including the strict limits a and b).

The expression composition "based on" should be understood as meaning a composition comprising the mixture and/or the reaction product of the various constituents used, some of these base constituents being capable of reacting or intended to react with one another, at least in part, during the various phases of manufacture of the composition, in particular during its crosslinking or vulcanization.

The compounds mentioned in the description can be of fossil origin or biobased. In the latter case, they may partially or completely result from biomass or be obtained from renewable starting materials resulting from biomass. Elastomers, plasticizers, fillers, and the like, are also concerned.

Diene elastomer should be understood as meaning an elastomer comprising diene monomer units, in particular 1,3-diene monomer units. The term "diene monomer unit" is understood to mean any unit which results from the insertion of a diene into a polymer chain and which contains a carbon-carbon double bond.

The term "1,3-dipolar compound" is understood according to the definition given by the IUPAC. By definition, it contains a dipole.

In the present patent application, carbon group is understood to mean a group which contains one or more carbon atoms. Group of atoms is also understood to mean a group formed by the linking together of several covalently bonded atoms.

In the present patent application, a carbon atom which is a member of the epoxide ring is described as tertiary carbon when the carbon atom is directly covalently bonded to two carbon atoms, one of which is also a member of the epoxide ring, and to the oxygen atom member of the epoxide ring. A carbon atom which is a member of the epoxide ring is described as quaternary carbon when the carbon atom is directly covalently bonded to three carbon atoms, one of which is also a member of the epoxide ring, and to the oxygen atom member of the epoxide ring.

In a known way, an epoxide group is a 3-membered ether ring, 2 members of which are two carbon atoms and the third member of which is an oxygen atom. The epoxide group in the 1,3-dipolar compound of use for the requirements of the invention is a 3-membered ether ring, a first member of which is a carbon atom exhibiting a connection to the dipole of the 1,3-dipolar compound and a second member of which is a tertiary or quaternary carbon. Preferably, the epoxide group is of formula (I).

In the formula (I), the symbol * represents a connection to the dipole; the symbols $X^1$, $X^2$ and $X^3$, which are identical or different, represent a hydrogen atom or a substituent group, and at least one of the symbols $X^1$, $X^2$ and $X^3$ is other than a hydrogen atom.

According to a preferential embodiment, $X^3$ represents a hydrogen atom, which amounts to saying that the first member of the epoxide ring is a tertiary carbon.

According to another preferential embodiment, $X^1$ represents a substituent group and $X^2$ represents a hydrogen atom, in which case the second member of the epoxide ring is a tertiary carbon.

According to another preferential embodiment of the invention, $X^1$ and $X^2$ each represent a substituent group, in which case the second member of the epoxide ring is a quaternary carbon.

Preferably, the substituent group represented by the symbols $X^1$, $X^2$ or $X^3$ is a carbon group, in particular a hydrocarbon group. The substituent group can be aliphatic or aromatic and linear, branched or cyclic. Substituent groups which are particularly suitable are alkyls and aryls, more particularly alkyls having from 1 to 6 carbon atoms, preferably methyl, or aryls having from 6 to 12 carbon atoms, preferably phenyl.

Preferably, the dipole of the 1,3-dipolar compound is a dipole containing at least one nitrogen atom, more preferentially a dipole selected from the group consisting of the nitrile oxide dipole, the nitrone dipole and the nitrilimine dipole. In other words, the 1,3-dipolar compound is more preferentially selected from the group consisting of nitrile oxides, nitrones and nitrilimines. Advantageously, the 1,3-dipolar compound is a nitrile oxide, in which case the dipole of the 1,3-dipolar compound is a nitrile oxide —C≡N→O.

According to one embodiment, the 1,3-dipolar compound comprises a benzene nucleus substituted by the dipole of the 1,3-dipolar compound and preferably also substituted in the position ortho to the dipole. Very advantageously, the 1,3 dipolar compound is an aromatic nitrile oxide, that is to say an aromatic compound substituted by a nitrile oxide dipole. Better still, the 1,3-dipolar compound is an aromatic nitrile monooxide, which corresponds to a compound which contains a single nitrile oxide dipole and which is an aromatic compound substituted by the nitrile oxide dipole.

According to a very specific embodiment of the invention, the 1,3-dipolar compound contains a unit of formula (II) in which four of the five symbols $R_1$ to $R_5$, which are identical or different, are each an atom or a group of atoms, and the fifth symbol represents a carbon chain which makes possible the connection to the epoxide group, it being known that at least one of $R_1$ and $R_5$ is other than a hydrogen atom.

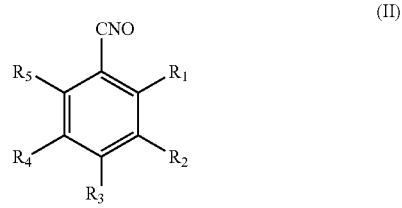

(II)

Group of atoms is understood to mean a sequence of atoms covalently bonded in order to form a chain. Two groups $R_i$ and $R_{i+1}$, for i an integer ranging from 1 to 4, can form, together with the carbon atoms of the benzene nucleus to which they are attached, a ring.

Preferably, $R_1$, $R_3$ and $R_5$ each represent a hydrocarbon group and $R_2$ or $R_4$ represents the fifth symbol. More preferentially, $R_1$, $R_3$ and $R_5$ each represent an alkyl, more preferentially still a methyl or an ethyl.

The carbon chain represented by the fifth symbol can be aliphatic or aromatic and linear, branched or cyclic, preferably saturated. The fifth symbol preferentially represents a carbon chain interrupted by one or more heteroatoms, preferably oxygen. Carbon chain is understood to mean a chain which comprises one or more carbon atoms. The carbon chain can be a hydrocarbon chain. The carbon chain can comprise one or more ether functional groups; in particular, the fifth symbol comprises a —CH$_2$O— unit, the methylene group being attached to the epoxide group.

Very advantageously, the 1,3-dipolar compound is a compound of formula (III), (IV) or (V).

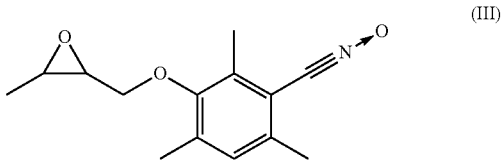

(III)

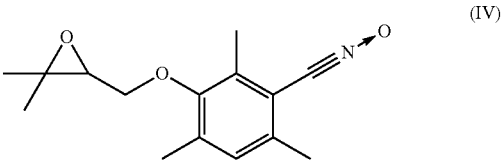

(IV)

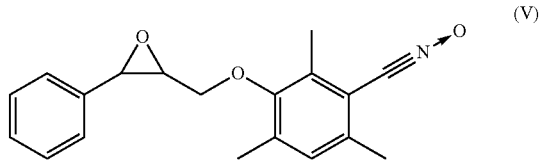

(V)

The content of 1,3-dipolar compound can vary to a large extent according to the application envisaged for the rubber composition. According to any one of the embodiments of the invention, the 1,3-dipolar compound is preferentially introduced into the rubber composition at a content ranging from 0.01 mol % to 5 mol %, more preferentially from 0.01 mol % to 1 mol %, more preferentially still from 0.1 mol % to 1 mol %. This content, expressed as molar percentage, is equivalent to the number of moles of 1,3-dipolar compound per 100 moles of diene monomer units of the diene polymer of use for the requirements of the invention.

The diene elastomer of use for the requirements of the invention can be:

(a) —any homopolymer of a conjugated diene monomer, in particular any homopolymer obtained by polymerization of a conjugated diene monomer having from 4 to 12 carbon atoms;

(b) —any copolymer obtained by copolymerization of one or more conjugated dienes with one another or with one or more vinylaromatic compounds having from 8 to 20 carbon atoms;

(c) —a ternary copolymer obtained by copolymerization of ethylene and of an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d) —a copolymer of isobutene and of isoprene (butyl rubber) and also the halogenated versions, in particular chlorinated or brominated versions, of this type of copolymer;

(e) —any copolymer obtained by copolymerization of one or more conjugated dienes with ethylene, an acyclic aliphatic α-monoolefin having from 3 to 18 carbon atoms or their mixture, such as, for example, those described in the documents WO 2005028526, WO 2004035639 and WO 2007054224.

Preferably, the diene elastomer is selected from the group of elastomers consisting of 1,3-butadiene homopolymers, isoprene homopolymers, 1,3-butadiene copolymers, isoprene copolymers and their mixtures.

The rubber composition comprises any type of "reinforcing" filler known for its abilities to reinforce a rubber composition which can be used in the manufacture of tyres, for example an organic filler, such as carbon black, a reinforcing inorganic filler, such as silica, with which is combined, in a known way, a coupling agent, or also a mixture of these two types of filler. Such a reinforcing filler typically consists of nanoparticles, the (weight-)average size of which is less than a micrometre, generally less than 500 nm, most often between 20 and 200 nm, in particular and more preferentially between 20 and 150 nm.

According to a specific embodiment of the invention, the reinforcing filler comprises a reinforcing inorganic filler, preferentially a silica. According to this embodiment, the reinforcing inorganic filler represents more than 50% by weight relative to the mass of the reinforcing filler of the rubber composition. It is then said that the reinforcing inorganic filler is predominant.

When it is combined with a predominant reinforcing inorganic filler, such as silica, the carbon black is preferably used at a content of less than 20 phr, more preferably of less than 10 phr (for example, between 0.5 and 20 phr, in particular between 2 and 10 phr). Within the intervals indicated, the colouring properties (black pigmenting agent) and UV-stabilizing properties of the carbon blacks are beneficial, without, moreover, adversely affecting the typical performance qualities contributed by the reinforcing inorganic filler.

Preferentially, the content of total reinforcing filler is between 30 and 160 phr, more preferentially between 40 phr and 160 phr. Below 30 phr, the reinforcement of the rubber composition is insufficient to contribute an appropriate level of cohesion or wear resistance of the rubber component of the tyre comprising this composition. More preferentially still, the content of total reinforcing filler is at least 50 phr. Above 160 phr, there exists a risk of increase in the hysteresis and thus in the rolling resistance of the tyres. For this reason, the content of total reinforcing filler is preferably within a range extending from 50 to 120 phr, in particular for use in a tyre tread. Any one of these ranges of content of total reinforcing filler can apply to any one of the embodiments of the invention.

In order to couple the reinforcing inorganic filler to the diene elastomer, use is made, in a well-known way, of an at least bifunctional coupling agent, in particular a silane, (or bonding agent) intended to provide a satisfactory connection, of chemical and/or physical nature, between the inorganic filler (surface of its particles) and the diene elastomer. Use is made in particular of organosilanes or polyorganosiloxanes which are at least bifunctional. More particularly, use is made of silane polysulfides, referred to as "symmetrical" or "asymmetrical" depending on their specific structure, such as described, for example, in Applications WO 03/002648 (or US 2005/016651) and WO 03/002649 (or US 2005/016650). Mention will more particularly be made, as examples of silane polysulfides, of bis(($C_1$-$C_4$)alkoxyl($C_1$-$C_4$)alkylsilyl($C_1$-$C_4$)alkyl) polysulfides (in particular disulfides, trisulfides or tetrasulfides), such as, for example, bis(3-trimethoxysilylpropyl) or bis(3-triethoxysilylpropyl) polysulfides. Use is made in particular, among these compounds, of bis(3-triethoxysilylpropyl) tetrasulfide, abbreviated to TESPT, of formula $[(C_2H_5O)_3Si(CH_2)_3S_2]_2$, or bis (triethoxysilylpropyl) disulfide, abbreviated to TESPD, of formula $[(C_2H_5O)_3Si(CH_2)_3S]_2$.

The content of coupling agent is advantageously less than 20 phr, it being understood that it is generally desirable to use as little as possible of it. Typically, the content of coupling agent represents from 0.5% to 15% by weight, with respect to the amount of inorganic filler. Its content is preferentially between 0.5 and 12 phr, more preferentially within a range extending from 3 to 10 phr. This content is easily adjusted by a person skilled in the art according to the content of inorganic filler used in the composition.

The rubber composition in accordance with the invention can also comprise, in addition to the coupling agents, coupling activators, agents for covering the inorganic fillers or more generally processing aids capable, in a known way, by virtue of an improvement in the dispersion of the filler in the rubber matrix and of a lowering of the viscosity of the compositions, of improving their ability to be processed in the raw state.

The rubber composition in accordance with the invention can also comprise all or a portion of the usual additives generally used in the elastomer compositions intended to constitute external mixtures for finished rubber articles, such as tyres, in particular for treads, such as, for example, plasticizers or extender oils, pigments, protective agents, such as antiozone waxes, chemical antiozonants or antioxidants, antifatigue agents, reinforcing resins (such as resorcinol or bismaleimide), methylene acceptors (for example phenolic novolak resin) or methylene donors (for example HMT or H3M), as described, for example, in Application WO 02/10269, a crosslinking system, vulcanization accelerators or retardants, or vulcanization activators.

The rubber composition preferably comprises a crosslinking system, which makes it possible to improve its elastic properties. The crosslinking system is preferably based on sulfur (or on a sulfur-donating agent) and on a primary vulcanization accelerator, that is to say a vulcanization system. Additional to this base vulcanization system are various known secondary vulcanization accelerators or vulcanization activators, such as zinc oxide, stearic acid or equivalent compounds, or guanidine derivatives (in particular diphenylguanidine), or else known vulcanization retarders, incorporated during the first non-productive phase and/or during the productive phase, as described subsequently. The sulfur is used at a preferred content of between 0.5 and 12 phr, in particular between 1 and 10 phr. The primary vulcanization accelerator is used at a preferential content of between 0.5 and 10 phr, more preferentially of between 0.5 and 5.0 phr. The crosslinking system can be based on polyacids, in particular diacids, as described in Patent Applications WO2014095582 and WO2014095585.

The rubber composition in accordance with the invention is manufactured in appropriate mixers, using two successive phases of preparation well known to a person skilled in the art: a first phase of thermomechanical working or kneading ("non-productive" phase) at high temperature, up to a maximum temperature of between 130° C. and 200° C., followed by a second phase of mechanical working ("productive" phase) up to a lower temperature, typically of less than 110° C., for example between 40° C. and 100° C., during which finishing phase the crosslinking system is incorporated.

According to a specific embodiment of the invention, the rubber composition in accordance with the invention can be manufactured by a process, which is another subject-matter of the invention, which comprises the following stages:

during a first "non-productive" stage, kneading the diene elastomer and the 1,3-dipolar compound as defined above by thermomechanically kneading, subsequently adding the reinforcing filler and, if appropriate, the other ingredients of the rubber composition, with the exception of the crosslinking system, by thermomechanically kneading until a maximum temperature of between 130° C. and 200° C. is reached, cooling the combined mixture to a temperature of less than 100° C., subsequently incorporating the crosslinking system, kneading everything up to a maximum temperature of less than 120° C.

The contact time between the diene elastomer and the 1,3-dipolar compound which are thermomechanically kneaded is adjusted as a function of the conditions of the thermomechanical kneading, in particular as a function of the temperature. The higher the temperature of the kneading, the shorter this contact time. Typically, it is from 1 to 5 minutes for a temperature of 100° C. to 130° C.

After the incorporation of all the ingredients of the rubber composition, the final composition thus obtained is subsequently calendered, for example in the form of a sheet or of a plaque, in particular for a laboratory characterization, or also extruded, in order to form, for example, a rubber profiled element used as rubber component in the preparation of the tyre, in particular a tyre tread.

The rubber composition in accordance with the invention can be either in the raw state (before crosslinking or vulcanization) or in the cured state (after crosslinking or vulcanization). It is preferentially used in a tyre, for example as semi-finished article.

A better understanding of the abovementioned characteristics of the present invention, and also others, will be obtained on reading the following description of several implementational examples of the invention, given by way of illustration and without limitation.

II. IMPLEMENTATIONAL EXAMPLES

II.1-Measurements and Tests Used

NMR Analysis:

The structural analysis and also the determination of the molar purities of the molecules synthesized are carried out by an NMR analysis. The spectra are acquired on a Bruker Avance 3400 MHz spectrometer equipped with a 5 mm BBFO Z-grad "broad band" probe. The quantitative $^1$H NMR experiment uses a simple 30° pulse sequence and a repetition time of 3 seconds between each of the 64 acquisitions. The samples are dissolved in deuterated dimethyl sulfoxide (DMSO). This solvent is also used for the lock signal. Calibration is carried out on the signal of the protons of the deuterated DMSO at 2.44 ppm with respect to a TMS reference at 0 ppm. The $^1$HNMR spectrum coupled with the 2D $^1$H/$^{13}$C HSQC and $^1$H/$^{13}$C HMBC experiments make possible the structural determination of the molecules (cf. tables of assignments). The molar quantifications are carried out from the quantitative 1D $^1$HNMR spectrum.

The determination of the molar content of grafted nitrile oxide compound is carried out by an NMR analysis. The spectra are acquired on a 500 MHz Bruker* spectrometer equipped with a "5 mm BBFO Z-grad CryoProbe". The quantitative $^1$H NMR experiment uses a simple 30° pulse sequence and a repetition time of 5 seconds between each acquisition. The samples are dissolved in deuterated chloroform (CDCl$_3$) with the aim of obtaining a "lock" signal. 2D NMR experiments have made it possible to confirm the nature of the grafted unit by virtue of the chemical shifts of the carbon and proton atoms.

Tensile Tests:

The elongations at break and the breaking stresses are measured by tensile tests according to French Standard NF T 46-002 of September 1988. All these tensile measurements are carried out under the standard conditions of temperature (23±2° C.) and of hygrometry (50%±5% relative humidity), according to French Standard NF T 40-101 (December 1979).

Dynamic Properties:

The dynamic properties tan(δ)max are measured on a viscosity analyser (Metravib VA4000) according to Standard ASTM D 5992-96. The response of a sample of vulcanized composition (cylindrical test specimen with a thickness of 4 mm and a cross-section of 400 mm$^2$), subjected to a simple alternating sinusoidal shear stress, at a frequency of 10 Hz, under standard temperature conditions (23° C.) according to Standard ASTM D 1349-99, is recorded. A strain amplitude sweep is carried out from 0.1% to 100% (outward cycle) and then from 100% to 0.1% (return cycle). The results made use of are the complex dynamic shear modulus (G*) at 25% strain, the loss factor tan(δ) and the difference in modulus (ΔG*) between the values at 0.1% and 100% strain (Payne effect). For the return cycle, the maximum value of tan(δ) observed, denoted tan(δ)max, is indicated.

Rheometry:

The measurements are carried out at 150° C. with an oscillating disc rheometer, according to Standard DIN 53529—Part 3 (June 1983). The measurements are processed according to Standard DIN 53529—Part 2 (March 1983). The change in the rheometric torque as a function of the time describes the change in the stiffening of the composition as a result of the vulcanization reaction and thus makes it possible to monitor the progress of the vulcanization. The minimum torque value Cmin is measured for each composition. The Cmin is representative of the viscosity in the raw state (before vulcanization) of the rubber composition and makes it possible to evaluate the processability of the rubber composition.

II.2-Synthesis of the 1,3-Dipolar Compounds

The following 1,3-dipolar compounds were prepared, respectively D-1, D-2, D-3 and D-4.

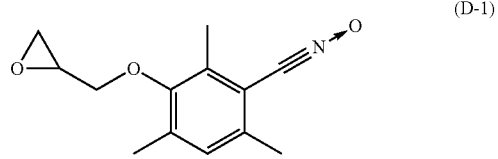

(D-1)

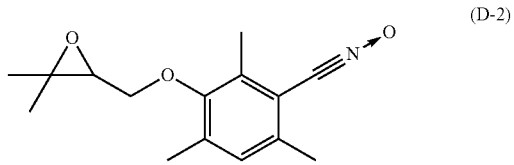

(D-2)

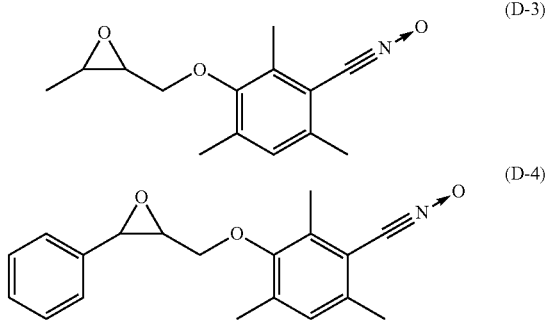

(D-3)

(D-4)

Synthesis of 3-hydroxy-2,4,6-trimethylbenzaldehyde (Target 1)

The target compound 1 (or A) is a common precursor used in the synthesis of some of the 1,3-dipolar compounds. It is synthesized according to the following scheme:

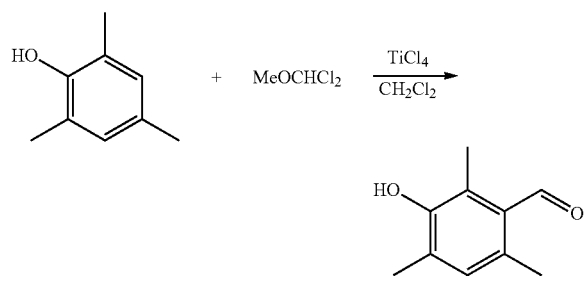

The target compound 1 can be obtained according to a procedure described in the paper Yakubov, A. P.; Tsyganov, D. V.; Belen'kii, L. I.; and Krayushkin, M. M., Bulletin of the Academy of Sciences of the USSR, *Division of Chemical Science (English Translation)*; Vol. 40; No. 7.2; (1991); pages 1427-1432; Izvestiya Akademii Nauk SSSR, Seriya Khimicheskaya; No. 7; (1991); pages 1609-1615.

Synthesis of 2,4,6-trimethyl-3-(oxiran-2-ylmethoxy)benzonitrile Oxide (D-1)

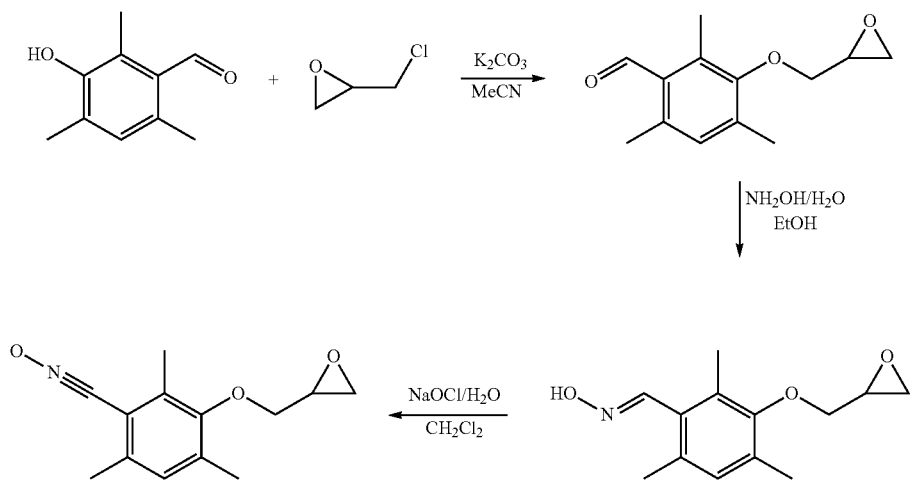

Synthesis of 2,4,6-trimethyl-3-(oxiran-2-ylmethoxy)benzaldehyde (Target 2)

Potassium carbonate (50.50 g, 0.365 mol) is added to a mixture of 3-hydroxy-2,4,6-trimethylbenzaldehyde (40.00 g, 0.244 mol) and epichlorohydrin (56.35 g, 0.609 mol) in acetonitrile (100 ml). The reaction medium is stirred at 60° C. for 3 hours and subsequently stirred at 70° C. for 2.5-3 hours. After returning to 40-50° C., the reaction mixture is diluted with a mixture of water (250 ml) and ethyl acetate (250 ml) and then kept stirred for 10 minutes. The organic phase is separated and washed with water (4 times with 125 ml). The solvent is evaporated under reduced pressure ($T_{bath}$ 37° C., 40 mbar). A red oil (66.43 g) is obtained. The byproduct of the reaction, 3,3'-((2-hydroxypropane-1,3-diyl)bis(oxy))bis(2,4,6-trimethylbenzaldehyde), is separated from the target product 2 by chromatography on a silica column (eluent: ethyl acetate/petroleum ether=1/4). After recovery of the fractions of the target product 2, the solvents are evaporated under reduced pressure ($T_{bath}$ 36° C., 21 mbar). Petroleum ether (120 ml) is added to the residue and the suspension is kept stirred at −18° C. for 2 hours. The precipitate is filtered off, washed on the filter with petroleum ether (40/60) (3 times 25 ml) and finally dried under atmospheric pressure at ambient temperature for 10-15 hours. A white solid (40.04 g, yield by weight of 75%) with a melting point of 52° C. is obtained. The molar purity is greater than 99% ($^1$H NMR). Tableau d'attribution :

| | δ $^1$H (ppm) | δ $^{13}$C (ppm) |
|---|---|---|
| 1 | 10.37 | 193.3 |
| 2 | / | 131.1 |
| 3 | / | 132.8 |

-continued

| | | |
|---|---|---|
| 4 | 2.4 | 19.2 |
| 5 | 6.94 | 131.3 |
| 6 | / | 136.3 |
| 7 | 2.2 | 16.1 |
| 8 | / | 153.4 |
| 9 | / | 135.7 |
| 10 | 2.4 | 11.7 |
| 11 | 3.50/4.00 | 73.4 |
| 12 | 3.29 | 49.6 |
| 13 | 2.60/2.76 | 42.9 |

Solvent DMSO

Synthesis of 2,4,6-trimethyl-3-(oxiran-2-ylmethoxy)benzaldehyde oxime (Target 3)

A solution of hydroxylamine (16.81 g, 0.254 mol, 50% in water, Aldrich) in ethyl alcohol (75 ml) is added at ambient temperature to a solution of 2,4,6-trimethyl-3-(oxiran-2-ylmethoxy)benzaldehyde (46.70 g, 0.212 mol) in ethyl alcohol (750 ml). The reaction medium is stirred at 23° C. ($T_{bath}$) for 3 hours. After evaporation of the solvent ($T_{bath}$ 24° C., 35 mbar), petroleum ether (40/60) (150 ml) is added. The precipitate is filtered off and washed on the filter with petroleum ether (100 ml). The crude product is dissolved in a mixture of ethyl acetate (650 ml) and petroleum ether (650 ml) at ambient temperature and this solution is filtered through a bed of silica gel (Ø 9 cm, 2.0 cm of $SiO_2$).

The solvents are evaporated ($T_{bath}$ 22-24° C.) and the target product 3 is dried under atmospheric pressure at ambient temperature. A white solid (43.81 g, yield by weight of 88%) with a melting point of 77° C. is obtained. The molar purity is greater than 99% ($^1H$ NMR).

Assignment Table

| | δ $^1H$ (ppm) | δ $^{13}C$ (ppm) |
|---|---|---|
| 1 | 8.2 | 147.3 |
| 2 | / | 129.1 |
| 3 | / | 129.2 |
| 4 | 2.18 | 20.1 |
| 5 | 6.85 | 130.2 |
| 6 | / | 130.3 |
| 7 | 2.15 | 15.7 |
| 8 | / | 153.1 |
| 9 | / | 131.7 |
| 10 | 2.18 | 13.1 |
| 11 | 3.48/3.96 | 73.3 |
| 12 | 3.27 | 49.6 |
| 13 | 2.60/2.76 | 42.8 |

Solvent DMSO

Synthesis of 2,4,6-trimethyl-3-(oxiran-2-ylmethoxy)benzonitrile Oxide (D-1)

An aqueous solution of NaOCl in water (62.9 g active Cl/l) (126 ml) is added dropwise over 10-15 minutes to a solution of 2,4,6-trimethyl-3-(oxiran-2-ylmethoxy)benzaldehyde oxime (17.00 g, 0.072 mol) in dichloromethane (350 ml) cooled down to 3° C. The temperature of the reaction medium remains between 3° C. and 5° C. The reaction medium is subsequently stirred at a temperature of 3-5° C. for 1 hour. The aqueous phase is separated and extracted with dichloromethane (25 ml). The combined organic phases are washed with water (3 times 75 ml). The solvent is evaporated at reduced pressure ($T_{bath}$ 22° C., 35 mbar). Petroleum ether (40/60) (90 ml) is added to this residue and the suspension is kept stirred at ambient temperature for 10-12 hours. The precipitate is filtered off, washed on the filter with petroleum ether (3 times with 30 ml) and finally dried under atmospheric pressure at ambient temperature for 10-15 hours. A white solid (15.12 g, yield by weight of 90%) with a melting point of 63° C. is obtained. The molar purity is greater than 99% ($^1H$ NMR). Tableau d'attribution :

| | δ $^1H$ (ppm) | δ $^{13}C$ (ppm) |
|---|---|---|
| 1 | 2.59/2.76 | 43.0 |
| 2 | 3.28 | 49.6 |
| 3 | 3.51/4.03 | 73.5 |
| 4 | / | 153.0 |
| 5 | / | 136.3 |
| 6 | 2.27 | 14.3 |
| 7 | / | 111.7 |
| 8 | / | / |
| 9 | / | 134.4 |
| 10 | 2.18 | 15.9 |
| 11 | 7.01 | 129.9 |
| 12 | / | 134.0 |
| 13 | 2.27 | 19.5 |

Synthesis of 2,4,6-trimethyl-3-(3-(3,3-dimethyloxiran-2-yl)propoxy)benzonitrile Oxide (D-2)

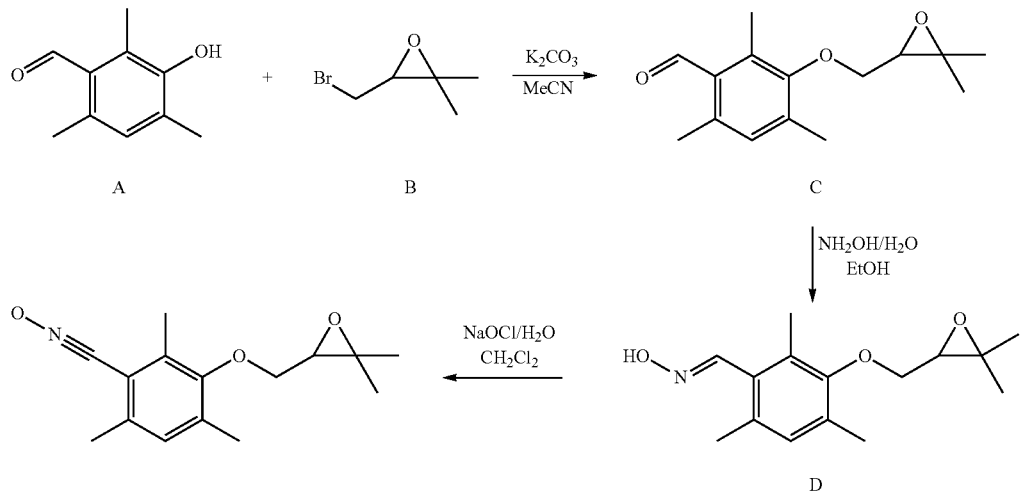

Synthesis of 3-(bromomethyl)-2,2-dimethyloxirane (B)

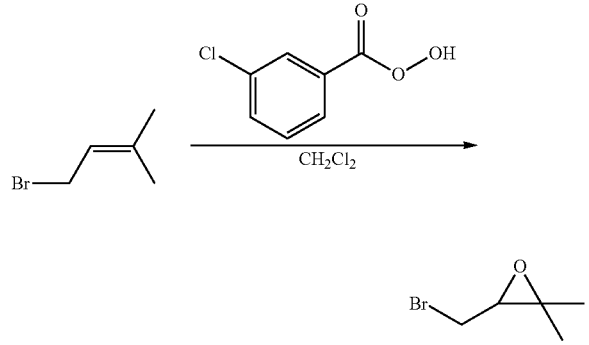

The compound B can be obtained according to a procedure described in the paper Shimizu, Hitoshi et al.; *Organic Process Research & Development*, 9(3), 278-287; 2005

Synthesis of 3-((3,3-dimethyloxiran-2-yl)methoxy)-2,4,6-trimethylbenzaldehyde (C)

Potassium carbonate (12.12 g, 0.877 mol) is added to a mixture of 3-hydroxy-2,4,6-trimethylbenzaldehyde (19.20 g, 0.117 mol) and 3-(bromomethyl)-2,2-dimethyloxirane (19.30 g, 0.117 mol) in acetonitrile (50 ml). The reaction medium is stirred at 60° C. ($T_{bath}$) for 10-11 hours. After returning to ambient temperature, the reaction mixture is diluted with a mixture of water (700 ml) and ethyl acetate (100 ml) and stirred for 10 minutes. The aqueous phase is separated and extracted with ethyl acetate (3 times 75 ml). The combined organic phases are washed twice with an NaOH solution (8.0 g in 100 ml of water) and water (5 times 75 ml). The solvent is evaporated under reduced pressure ($T_{bath}$ 35° C., 10 mbar). A light yellow oil (28.18 g, yield by weight of 97%) is obtained. The molar purity is greater than 85% ($^1$H NMR). The product C is used for the following stage without any additional purification.

Synthesis of 3-((3,3-dimethyloxiran-2-yl)methoxy)-2,4,6-trimethylbenzaldehyde oxime (D)

A solution of hydroxylamine (5.02 g, 0.760 mol, 50% in water, Aldrich) in ethyl alcohol (10 ml) is added at 40° C. ($T_{bath}$) to a solution of 3-((3,3-dimethyloxiran-2-yl)methoxy)-2,4,6-trimethylbenzaldehyde (11.8 g, 0.475 mol) in ethyl alcohol (25 ml). The reaction medium is stirred at 55° C. ($T_{bath}$) for 2.5-3.0 hours. After evaporation of the solvent ($T_{bath}$ 32° C., 26 mbar), a mixture of ethyl acetate (20 ml), petroleum ether (40/60) (30 ml) and water (10 ml) is added. The organic phase is subsequently separated and washed with water (10 ml). The solution is filtered through a bed of silica gel (Ø 3.5 cm, h=2.0 cm) and then the bed of silica gel is washed with a mixture of ethyl acetate (10 ml) and petroleum ether (20 ml). After evaporation of the

Assignment Table

| | δ $^1$H (ppm) | δ $^{13}$C (ppm) |
|---|---|---|
| 1 | 10.4 | 192.6 |
| 2 | / | 131.2 |
| 3 | / | 133.3 |
| 4 | 2.43 | 12 |
| 5 | / | 153.7 |
| 6 | 3.67 and 3.87 | 71.3 |
| 7 | 3.09 | 61.1 |
| 8 | / | 57.8 |
| 9 | 1.17 and 1.28 | 18.6 and 24.3 |
| 10 | / | 125.8 |
| 11 | 2.21 | 16.5 |
| 12 | 6.79 | 13.5 |
| 13 | / | 136.4 |
| 14 | 2.4 | 19.5 |

Solvent CDCl$_3$ solvents (T$_{bath}$ 33° C., 11 mbar), a colourless oil (10.33 g, yield by weight of 83%) is obtained. The molar purity is greater than 78% ($^1$H NMR) and 16% of EtOAc. The product D is used in the following stage without additional drying.

Assignment Table

| | δ $^1$H (ppm) | δ $^{13}$C (ppm) |
|---|---|---|
| 1 | 8.29 | 149.2 |
| 2 | / | 128.3 |
| 3 | / | 129.9 |
| 4 | 2.27 | 13.3 |
| 5 | / | 153.5 |
| 6 | 3.76 and 3.88 | 71.2 |
| 7 | 3.15 | 61.4 |
| 8 | / | 58 |
| 9 | 1.22 and 1.33 | 18.6 and 24.4 |
| 10 | / | 131.3 |
| 11 | 2.22 | 16.1 |
| 12 | 6.83 | 130.5 |
| 13 | / | 132.7 |
| 14 | 2.25 | 20.4 |

Solvent CDCl$_3$

Synthesis of 3-((3,3-dimethyloxiran-2-yl)methoxy)-2,4,6-trimethylbenzonitrile Oxide (D-2)

An aqueous solution of NaOCl in water (62.9 g of Cl/l) (65 ml) is added dropwise over 15 minutes to a solution of 3-((3,3-dimethyloxiran-2-yl)methoxy)-2,4,6-trimethylbenzaldehyde oxime (9.90 g, 0.367 mol) in dichloromethane (350 ml) cooled down to 1-3° C. The temperature of the reaction medium remains between 2-3° C. The reaction medium is subsequently stirred at 2-3° C. for 2 hours. The organic phase is separated and washed with water (3 times 50 ml). The solvent is evaporated at reduced pressure (T$_{bath}$ 21° C., 120 mbar). Petroleum ether (40/60) (15 ml) is added to this residue and the suspension is maintained at −18° C. for 2 hours. The precipitate is filtered off, washed on the filter with petroleum ether (3 times with 15 ml) and finally dried under atmospheric pressure at ambient temperature for 10-15 hours. A white solid (4.42 g, yield by weight of 45%) with a melting point of 84° C. is obtained. The molar purity is greater than 98% ($^1$H NMR).

Assignment Table

| | δ $^1$H (ppm) | δ $^{13}$C (ppm) |
|---|---|---|
| 1 | / | / |
| 2 | / | 112.7 |
| 3 | / | 134.2 |
| 4 | 2.35 | 14.8 |
| 5 | / | 153.4 |
| 6 | 3.93/3.71 | 71.9 |
| 7 | 3.11 | 61.2 |
| 8 | / | 57.8 |
| 9 | 1.22 and 1.33 | 24.5/18.8 |
| 10 | / | 134.2 |
| 11 | 2.23 | 16.5 |
| 12 | 6.86 | 130.2 |
| 13 | / | 137.2 |
| 14 | 2.32 | 20 |

Solvent CDCl$_3$

Synthesis of 2,4,6-trimethyl-3-(3-(3-methyloxiran-2-yl)propoxy)benzonitrile Oxide (D-3)

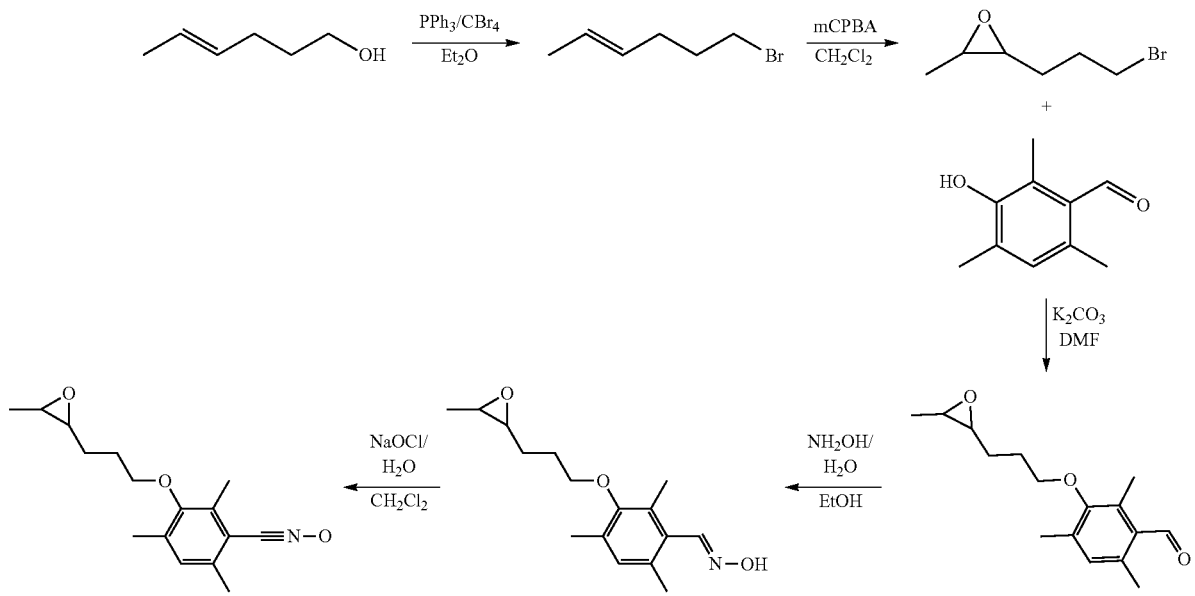

Synthesis of 6-bromohex-2-ene

This compound can be obtained, for example, according to a procedure described in the paper Nicolai, Stefano et al., *Tetrahedron*, 71(35), 5959-5964, 2015.

Synthesis of 2-(3-bromopropyl)-3-methyloxirane

This compound can be obtained, for example, according to a procedure described in the paper Hu, Shanghai; and Hager, Lowell P.; *Tetrahedron Letters*; Vol. 40; No. 9; (1999); pp. 1641-1644.

Synthesis of 2,4,6-trimethyl-3-(3-(3-methyloxiran-2-yl)propoxy)benzaldehyde

Potassium carbonate (6.01 g, 0.044 mol) is added to a mixture of 3-hydroxy-2,4,6-trimethylbenzaldehyde (10.00 g, 0.061 mol) and 2-(3-bromopropyl)-3-methyloxirane (10.39 g, 0.058 mol) in DMF (5 ml). The reaction medium is stirred at 80° C. ($T_{bath}$) for 1 hour and at 100° C. ($T_{bath}$) for 3 hours. After returning to ambient temperature, the reaction mixture is diluted with a mixture of water (75 ml) and methylene chloride (50 ml). The product is extracted with methylene chloride (2 times 10 ml). The combined organic phases are washed twice with an NaOH solution (4 g in 50 ml of water) and water (3 times with 15 ml). The solvent is evaporated under reduced pressure ($T_{bath}$ 45° C., 8 mbar). An oil (14.25 g, yield by weight of 93%) is obtained. The molar purity is greater than 85% ($^1$H NMR). The product is used for the following stage without additional purification.

Assignment Table

| | δ $^1$H (ppm) | δ $^{13}$C (ppm) |
|---|---|---|
| 1 | 10.46 | 193.2 |
| 2 | / | 131.7 |
| 3 | / | 133.8 |
| 4 | 2.45 | 19.9 |
| 5 | 6.83 | 131.9 |
| 6 | / | 137 |
| 7 | 2.22 | 16.8 |
| 8 | / | 154.4 |
| 9 | / | 136.5 |
| 10 | 2.44 | 12.3 |
| 11 | 3.67 | 72.2 |
| 12 | 1.89 | 26.7 |
| 13 | 1.62-1.79 | 28.7 |
| 14 | 2.66 | 59.3 |
| 15 | 2.75 | 54.5 |
| 16 | 1.25 | 17.6 |

Solvent CDCl$_3$

Synthesis of 2,4,6-trimethyl-3-(3-(3-methyloxiran-2-yl)propoxy)benzaldehyde Oxime A solution of hydroxylamine (5.13 g, 0.078 mol, 50% in water, Aldrich) in ethyl alcohol (10 ml) is added at 45° C. to a solution of 2,4,6-trimethyl-3-(3-(3-methyloxiran-2-yl)propoxy)benzaldehyde (14.00 g, 0.056 mol) in ethyl alcohol (40 ml). The reaction medium is stirred at 50° C. ($T_{bath}$) for 1.5 hours. After evaporation of the solvent ($T_{bath}$ 40° C., 45 mbar), methylene chloride (50 ml) is added and the solution is washed with water (3 times 15 ml). Subsequently, after evaporation of the solvent ($T_{bath}$ 40° C., 70 mbar), methylene chloride is added. The suspension is stirred at ambient temperature for 10 minutes and cooled down to −18° C. for 10-15 minutes. The precipitate is filtered off, washed on the filter three times with a mixture of methylene chloride (1 ml) and petroleum ether (4 ml) and finally dried under atmospheric pressure at ambient temperature. A white solid (10.02 g, yield by weight of 65%) with a melting point of 78° C. is obtained. The molar purity is greater than 90% ($^1$H NMR).

Assignment Table

| | δ $^1$H (ppm) | δ $^{13}$C (ppm) |
|---|---|---|
| 1 | 1.26 | 17.6 |
| 2 | 2.76 | 54.7 |
| 3 | 2.68 | 59.5 |
| 4 | 1.65/1.79 | 28.8 |
| 5 | 1.88 | 26.8 |
| 6 | 3.68 | 72.0 |
| 7 | / | 154.1 |
| 8 | / | 130.4 |
| 9 | 2.24 | 13.6 |
| 10 | / | 128.4 |
| 11 | 8.30 | 149.9 |
| 12 | / | 132.7 |
| 13 | 2.25 | 20.5 |
| 14 | 6.82 | 130.8 |
| 15 | / | 131.8 |
| 16 | 2.19 | 16.3 |

Solvent CDCl$_3$

Synthesis of 2,4,6-trimethyl-3-(3-(3-methyloxiran-2-yl)propoxy)benzonitrile Oxide (D-3)

An aqueous solution of NaOCl in water (4% of active chlorine, Aldrich) (17 ml) is added dropwise over 5 minutes to a solution of 2,4,6-trimethyl-3-(3-(3-methyloxiran-2-yl)propoxy)benzaldehyde oxime (3.35 g, 0.012 mol) in dichloromethane (50 ml) cooled down to 0° C. ($T_{bath}$). The temperature of the reaction medium remains between 3° C. and 5° C. The reaction medium is subsequently stirred at a temperature of 3-5° C. for 1 hour. The aqueous phase is separated and then extracted with dichloromethane (5 ml). The combined organic phases are washed with water (2 times 5 ml). The solvent is evaporated at reduced pressure ($T_{bath}$ 21° C., 16 mbar). Petroleum ether (40/60) (7 ml) is added to this residue and the suspension is stirred at ambient temperature for 10 minutes. The precipitate is filtered off, washed on the filter with petroleum ether (2 times 5 ml) and finally dried under atmospheric pressure at ambient temperature. A light yellow solid (2.49 g, yield by weight of 75%) with a melting point of 56° C. is obtained. The molar purity is greater than 94% ($^1$H NMR).

Assignment Table

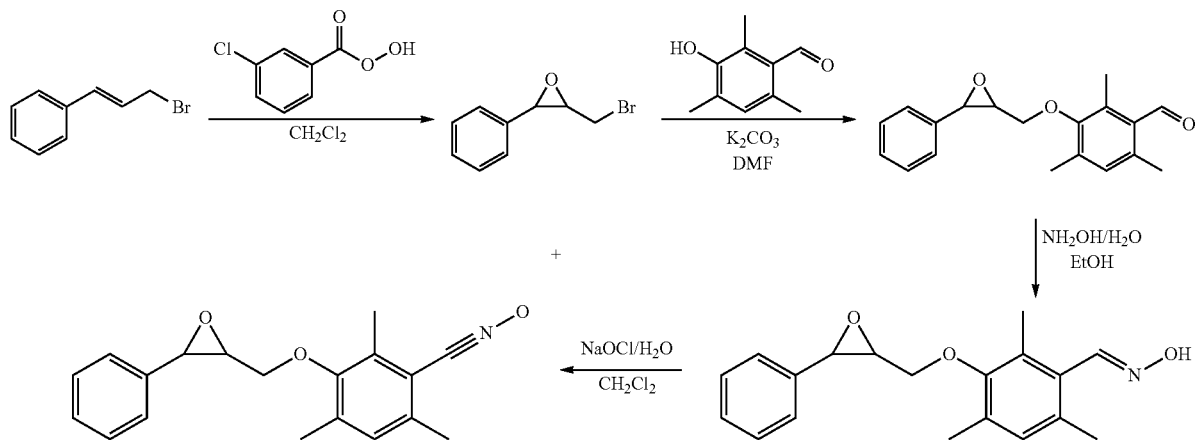

| | δ $^1$H (ppm) | δ $^{13}$C (ppm) |
|---|---|---|
| 1 | 1.26 | 17.6 |
| 2 | 2.75 | 54.5 |
| 3 | 2.66 | 59.3 |
| 4 | 1.60/1.80 | 28.7 |
| 5 | 1.88 | 26.8 |
| 6 | 3.68 | 72.2 |
| 7 | / | 153.9 |
| 8 | / | 137.1 or 134.6 |
| 9 | 2.31 | 14.9 |
| 10 | / | 112.8 |
| 11 | / | / |
| 12 | / | 137.1 or 134.6 |
| 13 | 2.31 | 20.3 |
| 14 | 6.84 | 130.3 |
| 15 | / | 134.6 |
| 16 | 2.19 | 16.5 |

Solvent CDCl$_3$

Synthesis of 2,4,6-trimethyl-3-((3-phenyloxiran-2-yl)methoxy)benzonitrile Oxide (D-4)

Synthesis of 2-(bromomethyl)-3-phenyloxirane

This compound can be obtained according to a procedure described in the paper Dickinson, Julia M. et al., *Chemical Society, Perkin Transactions 1: Organic and Bio-Organic Chemistry* (1972-1999), (4), 1179-84, 1990.

Synthesis of 2,4,6-trimethyl-3-((3-phenyloxiran-2-yl)methoxy)benzaldehyde

Potassium carbonate (8.51 g, 0.062 mol) is added to a mixture of 3-hydroxy-2,4,6-trimethylbenzaldehyde (13.50 g, 0.082 mol) and 2-(bromomethyl)-3-phenyloxirane (17.50 g, 0.082 mol) in DMF (8 ml). The reaction medium is stirred at 60° C. (T$_{bath}$) for 5-6 hours. After returning to 40-50° C., the reaction mixture is diluted with a mixture of water (200 ml) and ethyl acetate (70-80 ml). The target product is extracted with ethyl acetate (2 times 25 ml). The combined organic phases are washed with an NaOH solution (8 g in 70 ml of water) and water (4 times 25 ml). The solvent is evaporated under reduced pressure (T$_{bath}$ 34° C., 16 mbar). Petroleum ether (40/60) (50 ml) is added and the precipitate is filtered off, washed on the filter with a mixture of petroleum ether (15 ml) and ethyl acetate (1 ml) and finally dried under atmospheric pressure at ambient temperature.

A beige solid (13.28 g, yield by weight of 55%) with a melting point of 53° C. is obtained. The molar purity is greater than 90% ($^1$H NMR).

Assignment Table

| | δ $^1$H (ppm) | δ $^{13}$C (ppm) |
|---|---|---|
| 1/2 | 7.18 to 7.34 | 128.2/128.3 |
| 3 | | 125.5 |
| 4 | / | 136.2 |
| 5 | 3.81 | 55.9 |
| 6 | 3.35 | 60.2 |
| 7 | 3.84 and 4.04 | 72.5 |
| 8 | / | 153.8 |
| 9/13/16 | / | 132/133.7/136.7 |
| 10 | 2.5 | 12.2 |
| 11 | / | 131.5 |
| 12 | 10.48 | 193 |
| 14 | 2.48 | 19.8 |

| | | |
|---|---|---|
| 15 | 6.87 | 131.8 |
| 17 | 2.28 | 16.6 |

Solvent CDCl$_3$

Synthesis of 2,4,6-trimethyl-3-((3-phenyloxiran-2-yl)methoxy)benzaldehyde Oxime A solution of hydroxylamine (1.43 g, 0.022 mol, 50% in water, Aldrich) in ethyl alcohol (5 ml) is added at 45° C. to a solution of 2,4,6-trimethyl-3-((3-phenyloxiran-2-yl)methoxy)benzaldehyde (4.60 g, 0.016 mol) in ethyl alcohol (20 ml). The reaction medium is stirred at 50° C. (T$_{bath}$) for 1.5 hours. After returning to ambient temperature, water (3 ml) is added to the suspension and the suspension is maintained at −18° C. for 2 hours. The precipitate is filtered off, washed on the filter with a mixture of ethyl alcohol and water (3 ml/2 ml and 1 ml/4 ml) and finally dried under atmospheric pressure at ambient temperature. A white solid (3.62 g, yield by weight of 75%) with a melting point of 125° C. is obtained. The molar purity is greater than 97% ($^1$H NMR).

Assignment Table

| | δ $^1$H (ppm) | δ $^{13}$C (ppm) |
|---|---|---|
| 1/2 | 7.21 to 7.35 | 128/128.2 |
| 3 | | 125.4 |
| 4 | / | 136.2 |
| 5 | 3.81 | 56 |
| 6 | 3.35 | 60.3 |
| 7 | 3.85 and 4.02 | 72.2 |
| 8 | / | 153.4 |
| 9 | / | 130.2 |
| 10 | 2.29 | 13.1 |
| 11 | / | 128.2 |
| 12 | 8.31 | 149.6 |
| 13 | / | 132.9 |
| 14 | 2.27 | 20.3 |
| 15 | 6.85 | 130.7 |
| 16 | / | 131 |
| 17 | 2.24 | 16 |

Solvent CDCl$_3$

Synthesis of 2,4,6-trimethyl-3-((3-phenyloxiran-2-yl)methoxy)benzonitrile Oxide (D-4)

An aqueous solution of NaOCl in water (74.4 g of Cl/l) (48 ml) is added dropwise over 15 minutes to a solution of 2,4,6-trimethyl-3-((3-phenyloxiran-2-yl)methoxy)benzaldehyde oxime (10.20 g, 0.033 mol) in dichloromethane (150 ml) cooled down to 4° C. The temperature of the reaction medium remains between 3° C. and 5° C. The reaction medium is subsequently stirred at a temperature of 3-5° C. for 2.5 hours. The aqueous phase is separated and extracted with dichloromethane (15 ml). The combined organic solutions are washed with water (3 times 20 ml). The solvent is evaporated at reduced pressure (T$_{bath}$ 23° C., 22 mbar). Petroleum ether (40/60) (60 ml) is added and the suspension is stirred at ambient temperature for 10-15 minutes. The precipitate is filtered off, washed on the filter with petroleum ether (2 times with 20 ml) and finally dried under atmospheric pressure at ambient temperature. A white solid (8.35 g, yield by weight of 82%) with a melting point of 64° C. is obtained. The molar purity is greater than 98% ($^1$H NMR).

Assignment Table

| | δ $^1$H (ppm) | δ $^{13}$C (ppm) |
|---|---|---|
| 1/2 | 7.21 to 7.35 | 128.2/128.4 |
| 3 | | 125.4 |
| 4 | / | 136.1 |
| 5 | 3.79 | 55.8 |
| 6 | 3.33 | 60.1 |
| 7 | 3.82 and 4.05 | 72.5 |
| 8 | / | 153.3 |
| 9/13/16 | / | 130.3/134.4/137.3 |
| 10 | 2.36 | 14.6 |
| 11 | / | 112.8 |
| 12 | / | / |
| 14 | 2.33 | 20.1 |
| 15 | 6.87 | 130.2 |
| 17 | 2.25 | 16.4 |

Solvent CDCl$_3$

II.3-Preparation of the Rubber Compositions

Five rubber compositions are prepared, respectively C, I-1, I-2, I-3 and I-4. The formulations of the compositions appear in Table I.

The composition C is a control composition, since it is not based on a 1,3-dipolar compound. The composition I-n (n ranging from 1 to 4) is based on the dipole compound D-n.

The composition I-1 is a comparative composition, since the 1,3-dipolar compound used has an epoxide ring, a first member of which is a carbon atom exhibiting a connection to the dipole but a second member of which is neither a tertiary carbon nor a quaternary carbon. The compositions I-2 to I-4 are in accordance with the invention since each of the 1,3-dipolar compounds used has an epoxide ring, a first member of which is a carbon atom exhibiting a connection to the dipole and a second member of which is a tertiary carbon (I-3 and I-4) or a quaternary carbon (I-2).

The rubber compositions are prepared according to the following procedure:
The elastomer and, if appropriate, the 1,3-dipolar compound (0.5 mol %) are introduced into an internal mixer, the initial vessel temperature of which is approximately 80° C., and the combined mixture is kneaded for approximately one minute. The elastomer is a copolymer of 1,3-butadiene and of styrene having 26% of styrene unit and having 56% of 1,2-butadiene (vinyl) unit. The reinforcing filler, the silane and then, after kneading for 1 to 2 minutes, the various other ingredients, with the exception of the vulcanization system, are subsequently introduced. Thermomechanical working (non-productive phase) is then carried out in one stage (total duration of the kneading equal to approximately 5 minutes), until a maximum "dropping" temperature of 145° C. is reached. The mixture thus obtained is recovered and cooled and then the vulcanization system (sulfur) is added on an external mixer (homofinisher) at 25° C., everything being mixed (productive phase) for approximately 5 to 6 minutes. The mixture is subsequently calendered in the form of plaques (thickness of 2 to 3 mm) for measurement of the tensile properties and of the dynamic properties. The mixture is subsequently vulcanized, and its rheometric properties and its properties in the cured state are measured.

The results appear in Table II. The results are shown in base 100 with respect to the control composition (C): the value shown for a composition is the ratio of the value measured on the composition to the value measured on the control composition.

The vulcanized compositions I-2 to I-4 exhibit an elongation at break and a breaking stress which are improved in comparison with the composition I-1. These results are obtained without being to the detriment of the hysteresis properties, since the ΔG* and tan(δ)max values remain far below those of the control composition (C). The ΔC values, which are lower than that of composition C, corroborate an improvement in the interaction between the elastomer and the reinforcing filler.

It is also observed that the Cmin values of the compositions I-2 to I-4 are lower than that of the composition I-1, which indicates a decrease in the viscosity in the uncured state (before vulcanization) of the compositions and suggests the likelihood of a processing of the compositions I-2 to I-4 which is at least as easy as that of the composition C. This result is all the more surprising as an improvement in the interaction between the elastomer and the reinforcing filler has moreover been found.

To sum up, in comparison with the compositions not in accordance with the invention, the rubber compositions in accordance with the invention are characterized by an improved compromise between the properties at break, the hysteresis properties and the processing properties.

TABLE I

|  | Composition | | | | |
| --- | --- | --- | --- | --- | --- |
|  | C | I-1 | I-2 | I-3 | I-4 |
| SBR | 100 | | | | |
| SBR + D-1 | | 100 | | | |
| SBR + D-2 | | | 100 | | |
| SBR + D-3 | | | | 100 | |
| SBR + D-4 | | | | | 100 |
| Silica (1) | 60 | 60 | 60 | 60 | 60 |
| Silane (2) | 4.8 | 4.8 | 4.8 | 4.8 | 4.8 |
| Antioxidant (3) | 3 | 3 | 3 | 3 | 3 |
| Paraffin (4) | 1 | 1 | 1 | 1 | 1 |
| ZnO (5) | 2.7 | 2.7 | 2.7 | 2.7 | 2.7 |
| Stearic acid | 2.5 | 2.5 | 2.5 | 2.5 | 2.5 |

TABLE I-continued

|  | Composition | | | | |
| --- | --- | --- | --- | --- | --- |
|  | C | I-1 | I-2 | I-3 | I-4 |
| CBS (6) | 1.8 | 1.8 | 1.8 | 1.8 | 1.8 |
| Sulfur | 1.5 | 1.5 | 1.5 | 1.5 | 1.5 |

(1) 160 MP silica, sold by Solvay
(2) TESPT, sold by Evonik under the reference "Si69"
(3) N-(1,3-Dimethylbutyl)-N'-phenyl-p-phenylenediamine, from Flexsys
(4) Paraffin 6266 processing aid
(5) Zinc oxide
(6) N-Cyclohexyl-2-benzothiazolesulfenannide (Santocure from Flexsys)

TABLE II

|  | Composition | | | | |
| --- | --- | --- | --- | --- | --- |
|  | C | I-1 | I-2 | I-3 | I-4 |
| Elongation at break | 100 | 58 | 84 | 68 | 74 |
| Breaking stress | 100 | 90 | 111 | 97 | 97 |
| ΔG* | 100 | 71 | 79 | 88 | 88 |
| Tan(δ)max | 100 | 73 | 73 | 81 | 73 |
| Cmin | 100 | 110 | 74 | 74 | 84 |
| ΔC | 100 | 68 | 76 | 94 | 66 |

The invention claimed is:

1. A rubber composition based on at least one diene elastomer, a reinforcing filler and a 1,3-dipolar compound comprising an epoxide group, the epoxide group being a 3-membered ether ring in which a first member is a carbon atom exhibiting a connection to the dipole of the 1,3-dipolar compound and a second member is a tertiary or quaternary carbon.

2. The rubber composition according to claim 1, in which the 1,3-dipolar compound is selected from the group consisting of nitrile oxides, nitrones and nitrilimines.

3. The rubber composition according to claim 1, in which the 1,3-dipolar compound is a nitrile oxide.

4. The rubber composition according to claim 1, in which the compound is an aromatic nitrile monooxide.

5. The rubber composition according to claim 1, in which the 1,3-dipolar compound has, as formula, one of the formulae (III), (IV) or (V):

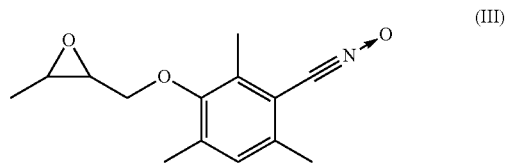

(III)

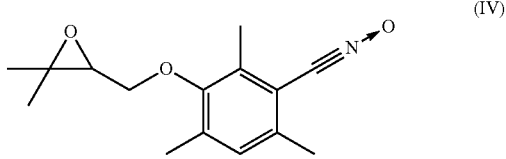

(IV)

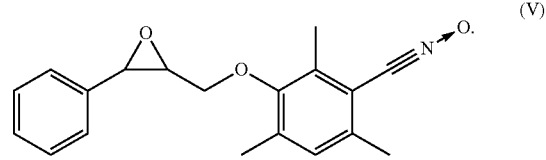

(V)

6. The rubber composition according to claim 1, in which the diene elastomer is selected from the group of elastomers consisting of 1,3-butadiene homopolymers, isoprene homopolymers, 1,3-butadiene copolymers, isoprene copolymers and their mixtures.

7. The rubber composition according to claim 1, in which the reinforcing filler comprises a reinforcing inorganic filler.

8. The rubber composition according to claim 1, which composition comprises a crosslinking system.

9. A rubber composition according to claim 1, in which the reinforcing filler comprises a silica.

10. The rubber composition according to claim 1, in which the epoxide group is of formula (I):

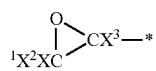
(I)

in which:
* represents a connection to the dipole,
$X^1$, $X^2$ and $X^3$, which are identical or different, represent a hydrogen atom or a substituent group, and
at least one of $X^1$, $X^2$ and $X^3$ is other than a hydrogen atom.

11. The rubber composition according to claim 1, in which the 1,3-dipolar compound comprises a benzene nucleus substituted by the dipole of the 1,3-dipolar compound.

12. The rubber composition according to claim 11, in which the benzene nucleus is substituted in the position ortho to the dipole.

13. The rubber composition according to claim 10, in which the substituent group is an alkyl or an aryl.

14. The rubber composition according to claim 1, in which the compound contains a unit of formula (II):

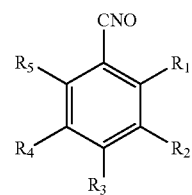
(II)

in which:
four of the five symbols $R_1$ to $R_5$, which are identical or different, are each an atom or a group of atoms, and the fifth symbol represents a carbon chain which makes possible the connection to the epoxide group, it being known that at least one of $R_1$ and $R_5$ is other than a hydrogen atom.

15. The rubber composition according to claim 14, in which $R_1$, $R_3$ and $R_5$ each represent a hydrocarbon group.

16. The rubber composition according to claim 14, in which the fifth symbol represents a carbon chain interrupted by one or more heteroatoms.

17. The rubber composition according to claim 14, in which the fifth symbol comprises a —$CH_2O$— unit, the methylene group being attached to the epoxide group.

18. A rubber composition according to claim 14, in which $R_1$, $R_3$ and $R_5$ each represent an alkyl group.

19. A rubber composition according to claim 14, in which the fifth symbol represents a carbon chain interrupted by one or more oxygen.

20. A tire which comprises the rubber composition defined in claim 1.

* * * * *